United States Patent
Chou et al.

(10) Patent No.: US 7,820,029 B2
(45) Date of Patent: Oct. 26, 2010

(54) PH MEASUREMENT SYSTEM AND METHOD FOR REDUCING TIME-DRIFT EFFECTS THEREOF

(75) Inventors: Jung-Chuan Chou, Yulin County (TW); Cheng-Hsin Liu, Pingtung Hsien (TW)

(73) Assignee: National Yunlin University of Science and Technology, Yunlin (TW)

( * ) Notice: Subject to any disclaimer, the term of this patent is extended or adjusted under 35 U.S.C. 154(b) by 609 days.

(21) Appl. No.: 11/822,961

(22) Filed: Jul. 11, 2007

(65) Prior Publication Data

US 2008/0067081 A1 Mar. 20, 2008

(30) Foreign Application Priority Data

Sep. 19, 2006 (TW) ............... 95134548 A

(51) Int. Cl.
*G01N 27/414* (2006.01)
*G01N 27/416* (2006.01)

(52) U.S. Cl. ............ 205/787.5; 204/433; 73/1.02

(58) Field of Classification Search ......... 204/400–435; 436/1–181; 73/53.01–64.56, 1.02; 438/49; 205/775–792; 257/253; 324/705, 71.5, 769
See application file for complete search history.

(56) References Cited

U.S. PATENT DOCUMENTS

| | | | |
|---|---|---|---|
| 4,657,658 A | | 4/1987 | Sibbald |
| 4,691,167 A | | 9/1987 | Vlekkert et al. |
| 4,879,517 A | | 11/1989 | Connery et al. |
| 5,130,265 A | | 7/1992 | Battilotti et al. |
| 5,309,085 A | * | 5/1994 | Sohn ..................... 257/253 |
| 6,617,190 B2 | | 9/2003 | Chou et al. |
| 2002/0006632 A1 | * | 1/2002 | Ponnampalam et al. ..... 435/7.92 |
| 2002/0180609 A1 | | 12/2002 | Ding et al. |
| 2003/0054177 A1 | | 3/2003 | Jin |
| 2003/0093011 A1 | | 5/2003 | Jalisi |
| 2004/0075578 A1 | | 4/2004 | Dudda et al. |
| 2005/0218976 A1 | * | 10/2005 | Haraguchi et al. ............. 330/9 |
| 2007/0138028 A1 | * | 6/2007 | Chodavarapu et al. ... 205/787.5 |

FOREIGN PATENT DOCUMENTS

WO WO 2004/093311 * 10/2004

OTHER PUBLICATIONS

Hong, Institute of Electronic Engineering National Yunlin University of Science and Technology, Master Thesis, pp. 1-160, 2004.*

(Continued)

*Primary Examiner*—Alexa D Neckel
*Assistant Examiner*—Jennifer Dieterle
(74) *Attorney, Agent, or Firm*—Muncy, Geissler, Olds & Lowe, PLLC

(57) ABSTRACT

A system of measuring pH of a solution having a calibration device to counteract time-drift effect. The calibration device of the system adjusts a compensation voltage to zero a measuring voltage of a first sensor and only respond to time-drift voltage of the first sensor. The calibration device has a differential operation amplifier receiving measuring voltages from the first sensor and a second sensor of the system to eliminate the time-drift voltages of the first and second sensors, thereby achieving calibration of the time-drift effects.

14 Claims, 5 Drawing Sheets

OTHER PUBLICATIONS

Ng., p. 520, Complete Guide to Semiconductor Devices, McGraw-Hill Inc. 1995.*

Cane et al., Microtechnologies for pH ISFET chemical sensors, Microelectronics Journal 28, 1997, 389-405.*

Wadika et al., PH Sensitive ISFETS Based on Titanium Nitride and Their Application to Battery Monitor, Proc. Transducers 91, San Francisco, CA, May 1991, pp. 222-224.*

* cited by examiner

PH MEASUREMENT SYSTEM AND METHOD FOR REDUCING TIME-DRIFT EFFECTS THEREOF

BACKGROUND OF THE INVENTION

1. Field of the Invention

The invention relates to a measuring system, and in particular to a system of measuring pHs of solutions and method for calibrating time-drift effects of sensors thereof.

2. Description of the Related Art

Extend Gate Ion Sensitive Field Effect Transistor (EGISFET) connects a sensing electrode, for example a titanium nitride electrode, to gate of metal oxide semiconductor field transistor (MOSFET). EGISFET can be fabricated using CMOS standard process, and is developed from Ion Sensitive Field Effect Transistor (ISFET).

Theorem and related knowledge of ISFET are detailed in the following list of documents:

1. U.S. Pat. No. 4,879,517, inventors: Connery, James G., Shaffer Jr., Earl W;
2. U.S. Pat. No. 6,617,190, inventors: Chou Jung Chuan, Chiang Jung Lung;
3. U.S. Pat. No. 5,309,085, inventor: Byung Ki Sohn;
4. U.S. Pat. No. 4,657,658, inventor: Alastair Slbbald;
5. US patent publication No. 20020180609, inventors: Kang Ding, W. E. JR. Seyfried, Zhong Zhang;
6. US patent publication No. 20030054177, inventor: Ping Jin;
7. US patent publication No. 20040075578, inventors: Olaf Dudda, Christian Oldendorf;
8. U.S. Pat. No. 4,691,167, inventors: Hendrik H. V. D. Vlekkert, Nicolaas F. de Rooy;
9. US patent publication No. 20030093011A1, inventors: Jalisi Marc Mehrzad;
10. U.S. Pat. No. 5,130,265, inventors: Massimo Battilotti, Giuseppina Mazzamurro, Matteo Giongo.

EGISFET comprises separated gate, is capable of being fabricated using CMOS standard process and has advantages of low cost, simple structure and easy package, making it suitable for biomedical application.

Many materials can act as detecting membranes for ISFETs, such as $Al_2O_3$, $Si_3N_4$, $Ta_2O_5$, amorphous $WO_3$ (a-$WO_3$), amorphous Si:H (a-Si:H) and others. Response time, hysteresis effect, time-drift effect, and light effect are important factors that influence performance of ISFET. EGISFET is developed from ISFET, having similar sensing principle, and therefore its performance is inevitably influenced by such non-ideal effects such as time-drift effect and hysterersis effect.

BRIEF SUMMARY OF INVENTION

Accordingly, an exemplary embodiment of the invention provides a system of measuring pHs of solutions, the system comprising: a first sensing unit provided in a solution, measuring pH of the solution to generate a first voltage; a second sensing unit provided in the solution, measuring pH of the solution to generate a second voltage, wherein the first and second sensing units having the same time-drift effect; and a calibration device for calibrating the time-drift effect of the first and second sensing units.

The calibration device comprises an offset voltage compensator outputting an adjustable compensation voltage, a first differential amplifier coupling the first voltage and the compensation voltage and outputting a third voltage, wherein the third voltage is substantially zeroed by adjusting the compensation voltage and only responsive to the time-drift effect of the first sensing unit, a second differential amplifier coupling the second voltage and a reference voltage, outputting a fourth voltage, and a third differential amplifier coupling the third voltage and the fourth voltage to counteract the time-drift effect of the first and second sensing units, thereby outputting a fifth voltage corresponding to pH of the solution.

Another exemplary embodiment of the invention provides a method for calibrating time-drift effect of a pH measuring system, providing a first sensing unit in a solution to measure pH of the solution and obtain a first voltage, providing a second sensing unit in the solution to measure pH of the solution and obtain a second voltage, the first and second sensing units having the same time-drift effect, and providing a calibration device to receive the first and second voltages to calibrate the time-drift effect of the first and second sensing units, wherein the calibration device comprises an offset voltage compensator, a first differential amplifier, a second differential amplifier and a third differential amplifier.

The method further comprises using the first differential amplifier to receive the first voltage and the compensation voltage output from the offset voltage compensator and output a third voltage, adjusting the compensation voltage to substantially to zero the third voltage and make the third voltage only respond to the time-drift effect of the first sensing unit, using the second differential amplifier to receive the second voltage and a reference ground and output a fourth voltage, and using the third differential amplifier to receive the third voltage and the fourth voltage to counteract the time-drift effect of the first and second sensing units, thereby outputting a calibrated fifth voltage corresponding to pH.

A detailed description is given in the following embodiments with reference to the accompanying drawings.

BRIEF DESCRIPTION OF DRAWINGS

The invention can be more fully understood by reading the subsequent detailed description and examples with references made to the accompanying drawings, wherein.

DETAILED DESCRIPTION OF INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
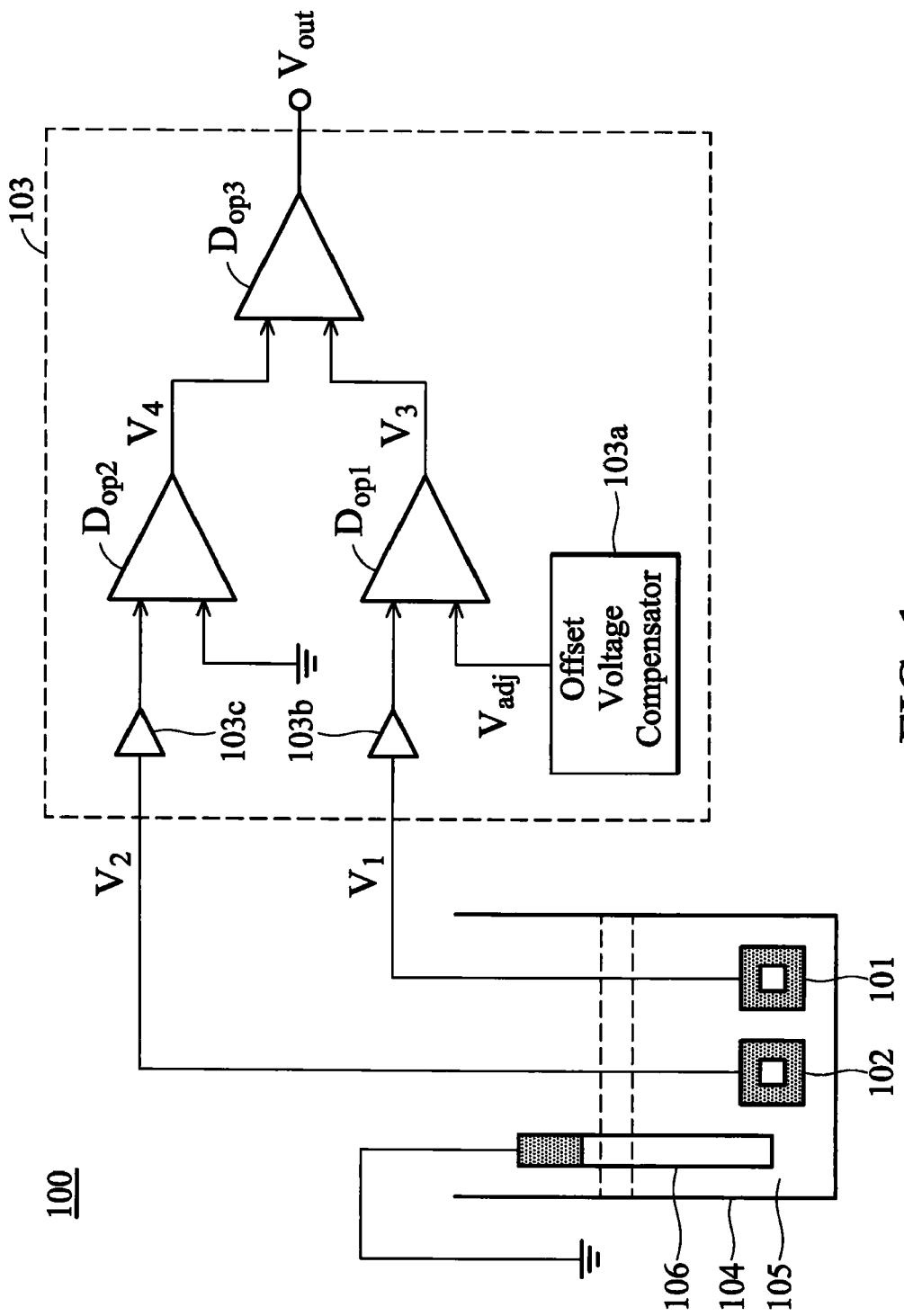
FIG. 1 shows block diagrams of a system of measuring pH values of solutions according to an exemplary embodiment of the invention.

FIG. 1 shows block diagrams of a system of measuring pH values of solutions according to an exemplary embodiment of the invention. The pH measuring system 100 comprises a first sensing unit 101, a second sensing unit 102, a calibration device 103, a light-isolating container 104 accommodating a testing solution 105, and a reference electrode 106. The reference electrode 106 is provided in the solution 105, connected to a reference ground through a conduction line to provide a ground reference voltage. In this embodiment, the reference electrode 106 is a silver/silver-chloride (Ag/AgCl) electrode. The light-isolating container 104 reduces light-sensitivity effect to the first and second sensing units 101 and 102.

The first and second sensing units 101 and 102 are provided in the solution 105 to measure pH of the solution 105 and generate a first voltage $V_1$ and a second voltage $V_2$, respectively. It is noted that the first and second sensing units 101 and 102 have the same time-drift effect.

The calibration device 103 comprises an offset voltage compensator 103a outputting an adjustable compensation voltage $V_{adj}$, a first differential amplifier $D_{op1}$ coupling the first voltage $V_1$ and the compensation voltage $V_{adj}$ and outputting a third voltage $V_3$, a second differential amplifier $D_{op2}$ coupling the second voltage $V_2$ and the reference ground, outputting a fourth voltage $V_4$, and a third differential amplifier $D_{op3}$ coupling the third voltage $V_3$ and the fourth voltage $V_4$ to counteract the time-drift effect of the first and second sensing units 101 and 102, thereby outputting an output voltage $V_{out}$ corresponding to pH of the solution 105.

The adjustable compensation voltage $V_{adj}$ is controlled by the offset voltage compensator 103a to zero the third voltage $V_3$ such that the third voltage $V_3$ merely responds to the time-drift effect (or time-drift voltage) of the first sensing unit 101. The fourth voltage $V_4$ responds to combination of pH of the solution 105 and the time-drift effect (time-drift voltage) of the second sensing unit 102. Therefore, the third differential amplifier $D_{op3}$ can eliminate the common time-drift effect of the first and second sensing units 101 and 102 and output the output voltage $V_{out}$ corresponding to pH of the solution, thereby achieving calibration to time-drift effect.

Figure 2:
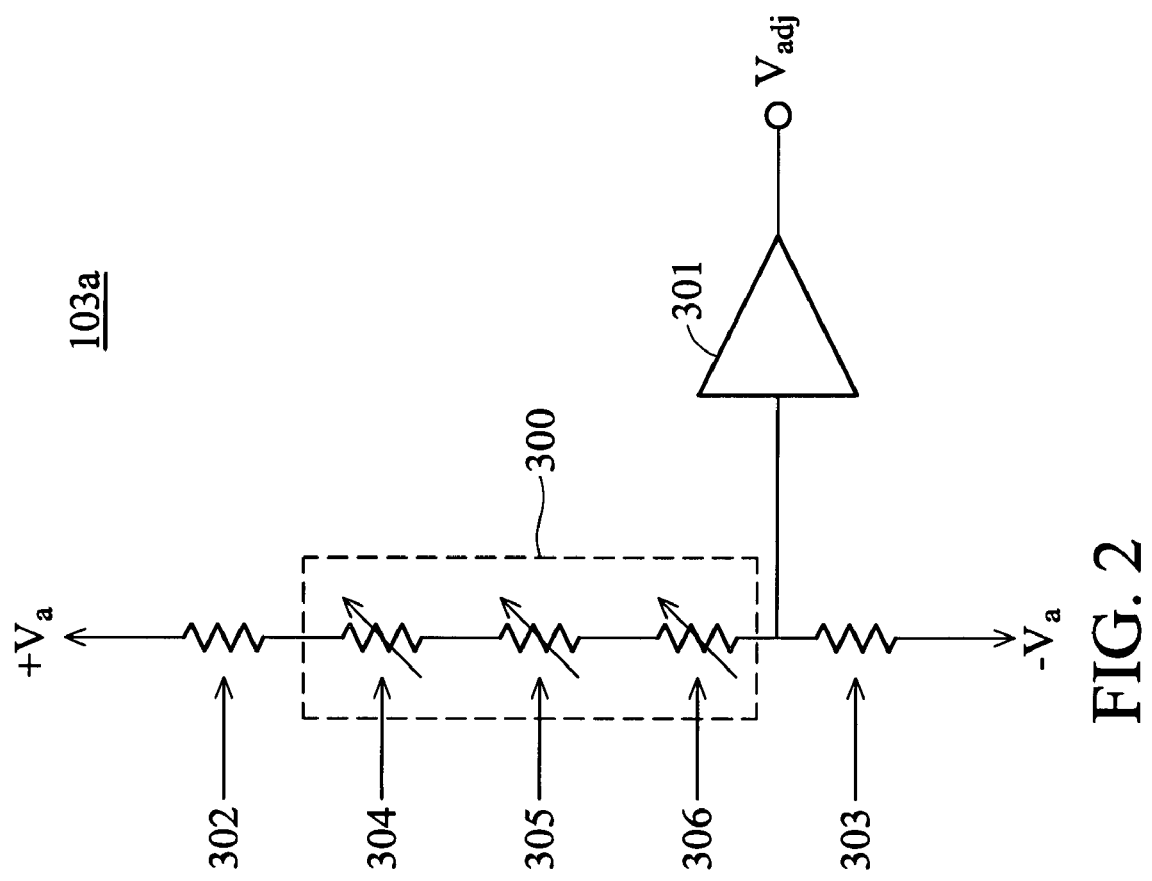
FIG. 2 shows a possible embodiment of the offset voltage compensator of the pH measuring system.

The offset voltage compensator 103a comprises at least a resistor, a variable resistive unit and a buffer; wherein the variable resistive unit comprises at least a variable resistor connected in series with the resistor, and an output of the buffer is coupled to a connection node of the resistor and the variable resistor. FIG. 2 shows a possible embodiment of the offset voltage compensator 103a. In FIG. 2, the offset voltage compensator 103a comprises a variable resistive unit 300 having three variable resistors 304 to 306 connected in series, two resistors 302 and 303, and a buffer 301. The variable resistive unit 300 and the resistors 302 and 303 are connected in series and provided between two voltage nodes $V_a$ and $-V_a$. The adjustable compensation voltage $V_{adj}$ can be controlled by changing resistances of the variable resistors 304 to 306.

The pH measuring system 100 further comprises a first buffer 103b coupled between the first sensing unit 101 and the first differential amplifier $D_{op1}$ and a second buffer 103c coupled between the second sensing unit 102 and the second differential amplifier $D_{op2}$, to increase input impedances of the first and second differential amplifiers $D_{op1}$ and $D_{op2}$. In this embodiment, the first and second sensing units 101 and 102 are EGISFETs and are manufactured using the same fabricating process and packaging condition. In addition, electrodes connecting to gates of the EGISFETs of the first and second sensing units 101 and 102 are titanium nitride electrodes.

A 1.0 cm×1.0 cm silicon wafer is used as a substrate to form the EGISFETs with titanium nitride gate electrodes. The substrate is cleaned in alcohol or deionized water (DI water) and cleaned by an ultrasonic oscillator. Then, nitrogen gas is sprayed to clean the surface of the substrate to ensure no water remained on the substrate. Titanium nitride electrode (or membrane) of the EGISFET is formed using sputtering with titanium target material of pure grade 99.995% and mixed gas of argon (Ar) gas and nitrogen gas ($N_2$) with 80 sccm and 10 sccm, respectively. The vacuum (or atmosphere pressure) inside the process chamber is adjusted to $10^{-6}$ Torr before deposition of titanium nitride. Further, surface of the titanium target is cleaned using RF power of 150 W for 10 minutes at ambient of 10 m Torr to prevent oxide thereon from being sputtered to the substrate.

After sputtering, the wafer is cleaned in deionized water and cleaned by ultrasonic oscillator to remove dust and particles therefrom. The titanium nitride membrane formed on the 1.0 cm×1.0 cm substrate is divided into four 0.5 cm×0.5 cm units. The four units are packaged to form four titanium nitride electrodes, such that the titanium nitride electrodes and the EGISFETs with such electrodes have the same time-drift effect.

Figure 3:
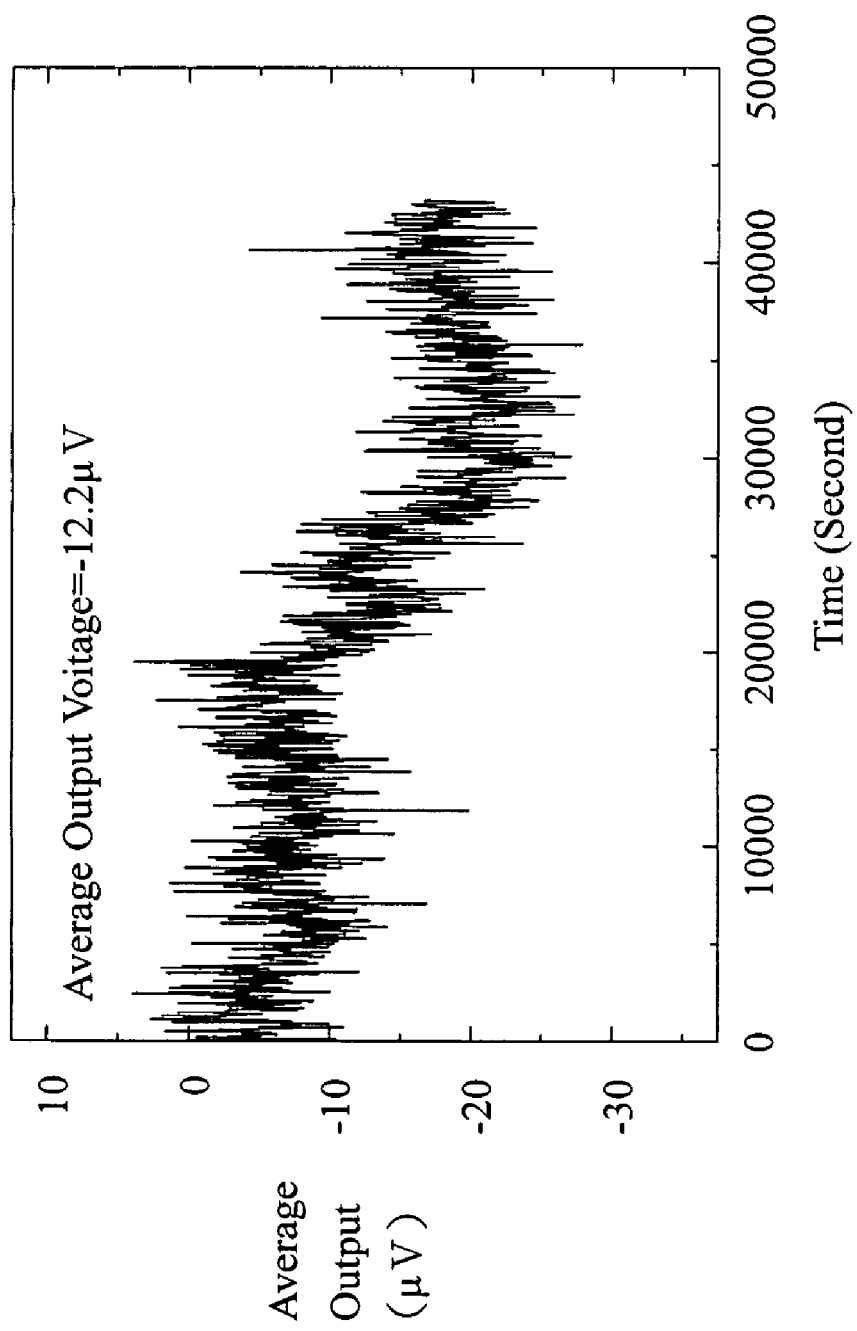
FIG. 3 shows a relation curve of the output voltage $V_{out}$ of the calibration device with respect to time.

Long time-drift experiment is carried out to test stability of the calibration device 103 of the pH measuring system 100. First, input terminals of the first and second differential amplifiers $D_{op1}$ and $D_{op2}$ are connected to reference ground. Then, the output voltages $V_{out}$ of the third differential amplifier $D_{op3}$ are recorded for a long time, obtaining a relation curve of the output voltage $V_{out}$ with respect to time (i.e., voltage-time relation curve) as shown in FIG. 3. Average drift voltage of the calibration device 103 can be obtained from the recorded output voltages $V_{out}$ in FIG. 3. The average drift voltage of the calibration device 103 is only about −12.2 μV, much less than the drift voltage of the sensing electrodes, so as to not be considered.

Figure 4:
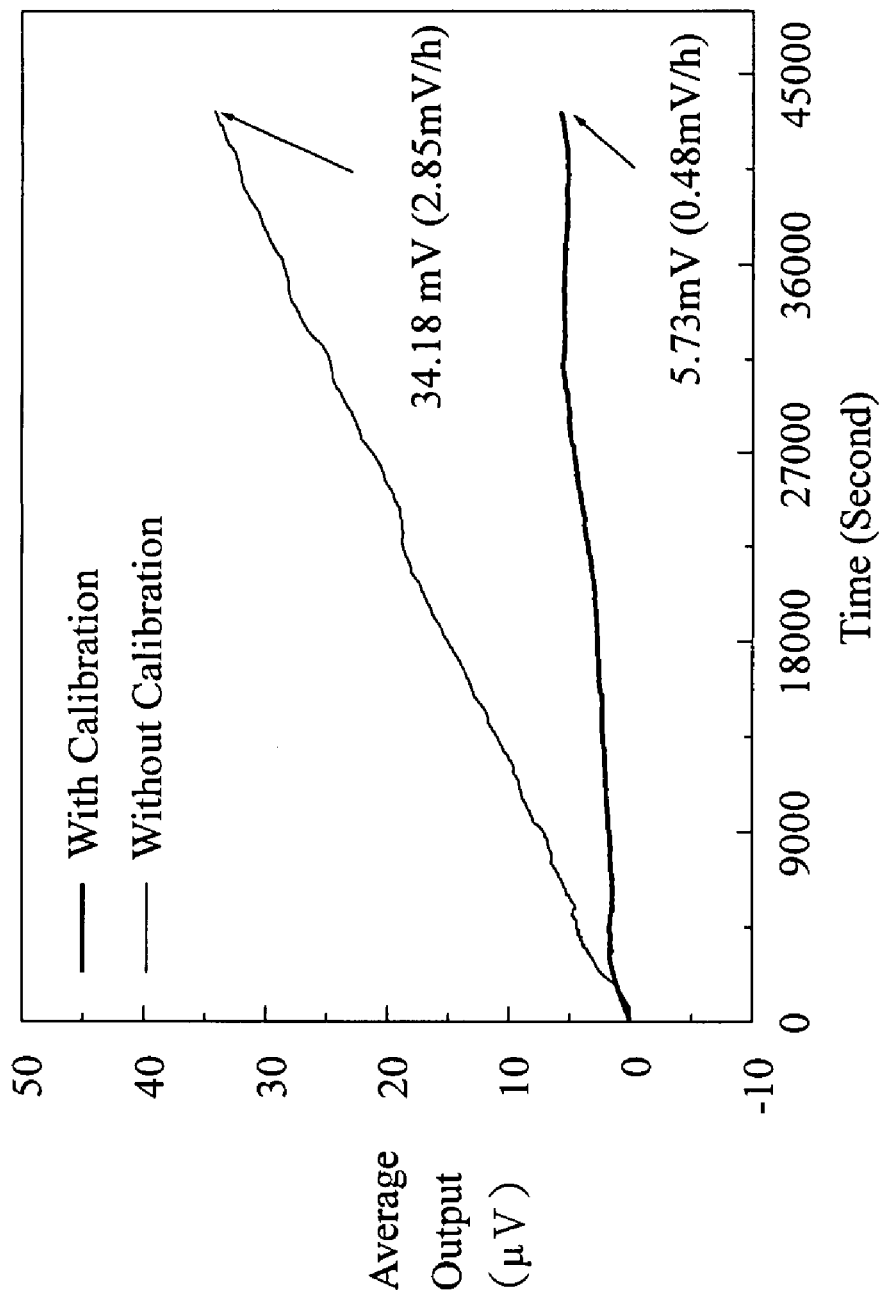
FIG. 4 shows responses of an original time-drift output voltage including original time-drift voltage and a calibrated output voltage including calibrated time-drift voltage, where both output voltages are respect to pH 6.

FIG. 4 shows responses of an original time-drift output voltage including original time-drift voltage and a calibrated output voltage including calibrated time-drift voltage, where both output voltages are respect to pH 6. It can be seen that time-drift voltage of the original output voltage without calibration is reduced from 34.18 mV (2.85 mV/H) to 5.73 mV (0.48 mV/H).

In addition, a method of measuring sensitivity of a sensing electrode for use in the pH measuring system 100 is disclosed. The method comprises using titanium nitride as electrodes of the first and second sensing units 101 and 102, contacting the titanium nitride electrodes with a test solution, changing pHs of the test solution at a fixed temperature, using the calibration device to measure pH and recording the output voltages $V_{out}$ output from the calibration device 103, obtaining a voltage-time relation curve at different pH levels, and obtaining sensitivity of the titanium nitride electrodes according to the voltage-time relation curve.

Figure 5:
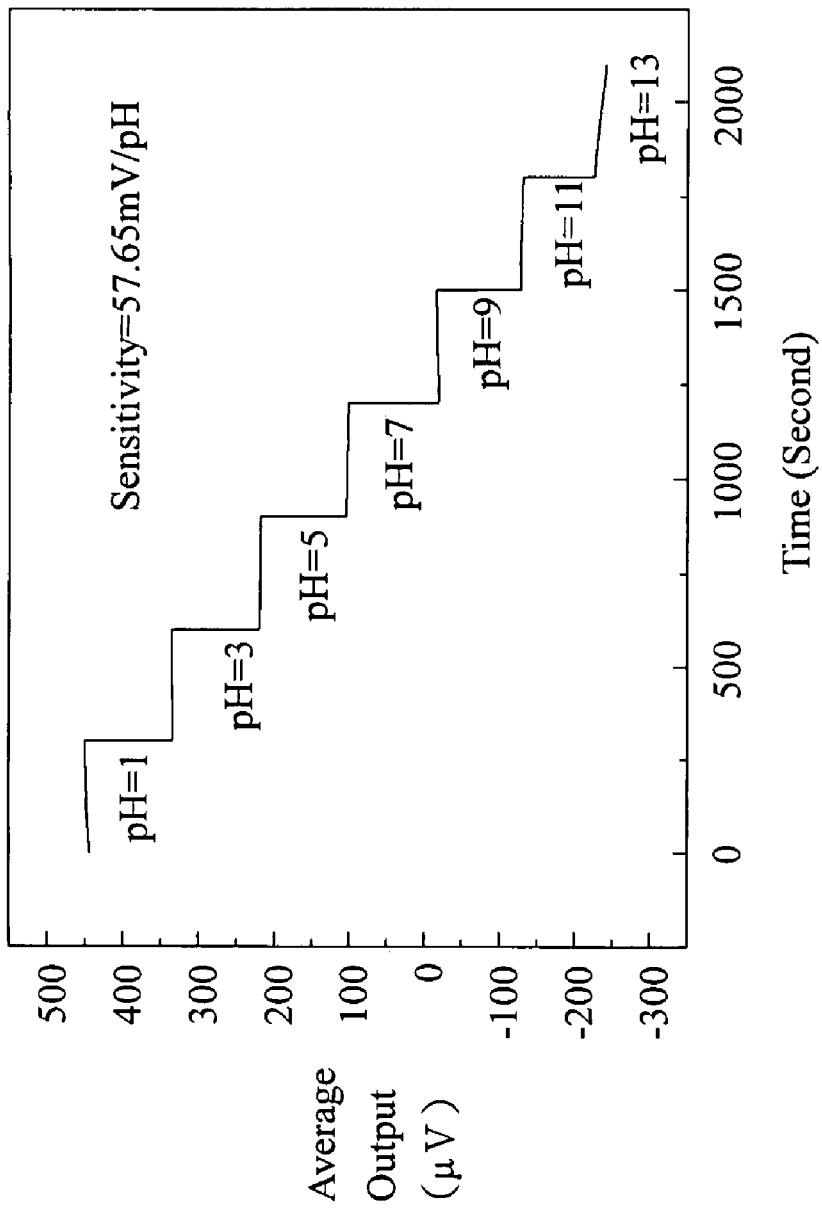
FIG. 5 shows a voltage-time relation curve at different pH values using the pH measuring system 100.

FIG. 5 shows a voltage-time relation curve at different pH levels using the pH measuring system 100. The sensitivity (S=V/pH) of the sensing units or electrodes can be obtained from FIG. 5 and is about 57.65 mV/pH.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A system of measuring pH of solutions, comprising:
a first sensing unit provided in a solution, measuring pH of the solution to generate a first voltage;
a second sensing unit provided in the solution, measuring pH of the solution to generate a second voltage; the first and second sensing units having the same time-drift effect; and a calibration device comprising:
- an offset voltage compensator outputting an adjustable compensation voltage;
- a first differential amplifier coupling the first voltage and the compensation voltage and outputting a third voltage; wherein the calibration device is configured to substantially zero the third voltage by adjusting the compensation voltage so that the third voltage is only responsive to the time-drift effect of the first sensing unit;
- a second differential amplifier coupling the second voltage and a reference voltage, outputting a fourth voltage; and
- a third differential amplifier coupling the third voltage and the fourth voltage to counteract the time-drift effect of the first and second sensing units, thereby outputting a fifth voltage corresponding to pH of the solution.

2. The system as claimed in claim 1, further comprising a first buffer coupled between the first sensing unit and the first differential amplifier, and a second buffer coupled between the second sensing unit and the second differential amplifier.

3. The system as claimed in claim 1, further comprising a light-isolating container accommodating the solution for reducing light-sensitivity effect to the first and second sensing units.

4. The system as claimed in claim 1, wherein the offset voltage compensator comprises at least a resistor, a variable resistive unit and a buffer; wherein the variable resistive unit comprises at least a variable resistor connected in series with the resistor, and an output of the buffer is coupled to a connection node of the resistor and the variable resistor.

5. The system as claimed in claim 1, wherein each of the first and second sensing units comprises an Extended Gate Ion Sensitive Field Effect Transistor (EGISFET).

6. The system as claimed in claim 5, wherein the EGISFETs of the first and second sensing units are fabricated using the same process and packaging condition, and wherein the sensing electrodes of the EGISFETs are titanium nitride electrodes.

7. The system as claimed in claim 1, further comprising a reference electrode provided in the solution and coupled to a reference ground to provide a ground reference voltage.

8. The system as claimed in claim 7, wherein the reference electrode is a silver/silver-chloride (Ag/AgCl) electrode.

9. A method of measuring sensitivity of a sensing electrode, for the system of measuring pH values of solution as claimed in claim 1, the method comprising:
- using titanium nitride as electrodes of the first and second sensing units; contacting the titanium nitride electrodes with a test solution;
- changing pH settings of the test solution at a fixed temperature, using the calibration device to measure pH and recording the fifth voltages output from the calibration device, thereby obtain a voltage-time relation curve at different pH levels; and
- obtaining sensitivities of the titanium nitride electrodes according to the voltage-time relation curve.

10. A method for calibrating time-drift effect of a pH measuring system, comprising:
- providing a first sensing unit in a solution to measure pH of the solution and obtain a first voltage;
- providing a second sensing unit in the solution to measure pH of the solution and obtain a second voltage; wherein the first and second sensing units have the same time-drift effect;
- providing a calibration device to receive the first and second voltages to calibrate the time-drift effect; the calibration device comprising an offset voltage compensator, a first differential amplifier, a second differential amplifier and a third differential amplifier;
- using the first differential amplifier to receive the first voltage and an adjustable compensation voltage output from the offset voltage compensator and output a third voltage;
- adjusting the compensation voltage to substantially zero the third voltage and make the third voltage only respond to the time-drift effect of the first sensing unit;
- using the second differential amplifier to receive the second voltage and a reference ground and output a fourth voltage; and
- using the third differential amplifier to receive the third voltage and the fourth voltage to counteract the time-drift effect of the first and second sensing units, thereby outputting a calibrated fifth voltage corresponding to pH.

11. The method as claimed in claim 10, wherein each of the first and second sensing units comprises an Extended Gate Ion Sensitive Field Effect Transistor (EGISFET).

12. The method as claimed in claim 11, wherein the EGISFETs of the first and second sensing units are fabricated using the same process and packaging condition, and sensing electrodes of the EGISFETs are titanium nitride electrodes.

13. The method as claimed in claim 10, further comprising providing a reference electrode in the solution, and coupling the reference electrode to the reference ground to provide a ground reference voltage.

14. The method as claimed in claim 13, wherein the reference electrode is a silver/silver-chloride (Ag/AgCl) electrode.

* * * * *